(12) United States Patent
Bidard-Michelot et al.

(10) Patent No.: US 10,577,668 B2
(45) Date of Patent: Mar. 3, 2020

(54) HYPER-PRODUCING TRICHODERMA REESEI STRAIN HAVING AN ENHANCED BETA-GLUCOSIDASE ACTIVITY

(71) Applicant: IFP Energies Nouvelles, Rueil Malmaison (FR)

(72) Inventors: Frédérique Bidard-Michelot, L'Etang la Ville (FR); Laetitia Chan Ho Tong, Bry sur Marne (FR); Antoine Margeot, Paris (FR); Céline Cohen, Paris (FR)

(73) Assignee: IFP Energies Nouvelles, Rueil Malmaison (FR)

( * ) Notice: Subject to any disclaimer, the term of this patent is extended or adjusted under 35 U.S.C. 154(b) by 0 days.

(21) Appl. No.: 16/142,929

(22) Filed: Sep. 26, 2018

(65) Prior Publication Data

US 2019/0100814 A1    Apr. 4, 2019

(30) Foreign Application Priority Data

Sep. 29, 2017   (FR) ...................................... 17 59144

(51) Int. Cl.

| | | |
|---|---|---|
| *C12P 7/00* | (2006.01) | |
| *C12R 1/885* | (2006.01) | |
| *C12N 1/14* | (2006.01) | |
| *C12N 9/42* | (2006.01) | |
| *C10L 1/02* | (2006.01) | |
| *C12P 7/06* | (2006.01) | |

(52) U.S. Cl.
CPC ................ *C12R 1/885* (2013.01); *C10L 1/02* (2013.01); *C12N 1/14* (2013.01); *C12N 9/2445* (2013.01); *C12P 7/06* (2013.01); *C12Y 302/01021* (2013.01); *C10L 2200/0469* (2013.01); *C10L 2290/26* (2013.01)

(58) Field of Classification Search
None
See application file for complete search history.

(56) References Cited

U.S. PATENT DOCUMENTS

2019/0100814 A1* 4/2019 Bidard-Michelot ...... C10L 1/02

FOREIGN PATENT DOCUMENTS

| WO | 2015/051012 A2 | 4/2015 |
| WO | 2015/086701 A1 | 6/2015 |

OTHER PUBLICATIONS

Seidl et al., "Sexual development in the industrial workhorse Trichoderma reesei," PNAS, 106: 13909-13914 (2009).
Schuster et al., "A versatile toolkit for high throughput functional genomics with Trichoderma reesei," Biotechnology for Biofuels, 5: 1-10 (2012).
Li et al., "A β-glucosidase hyper-production Trichoderma reesei mutant reveals a potential role of cel3D in cellulase production," Microbial Cell Factories, 15: 151 (2016).
Preliminary Search Report issued in corresponding French Patent Application No. 1759144 dated Apr. 26, 2018.

* cited by examiner

*Primary Examiner* — Hope A Robinson
(74) *Attorney, Agent, or Firm* — Morgan, Lewis & Bockius LLP

(57) ABSTRACT

The present invention relates to a *Trichoderma reesei* strain which is hyper-producing and which has enhanced β-glucosidase activity, as well as the use of said strain.

2 Claims, 3 Drawing Sheets

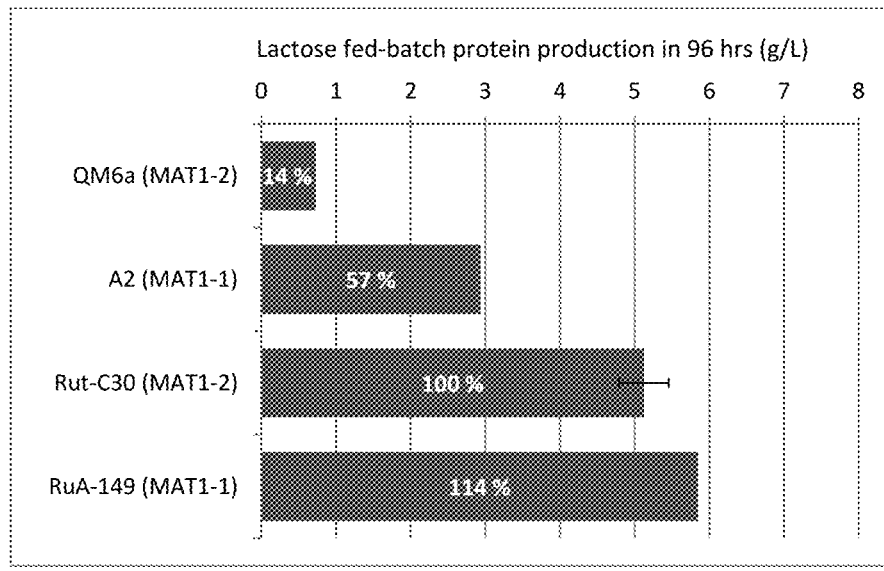
Figure 1: Fed-flask protein production
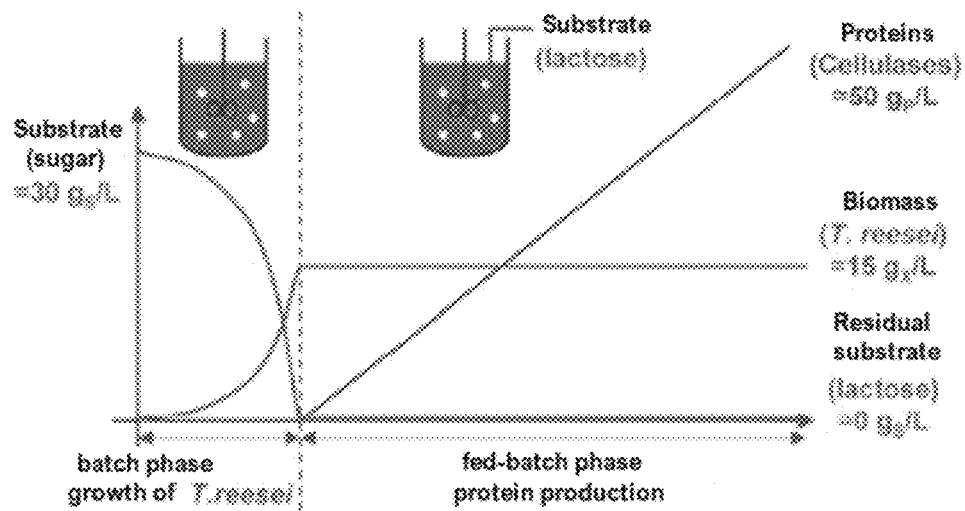
Figure 2: Cellulase production process principle

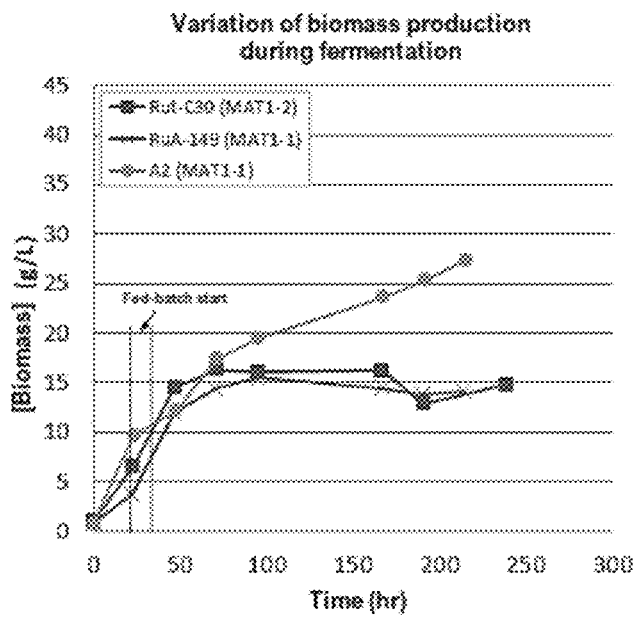
Figure 3A: Evaluation of quantity of biomass produced during fermentation in a DASGIP bioreactor
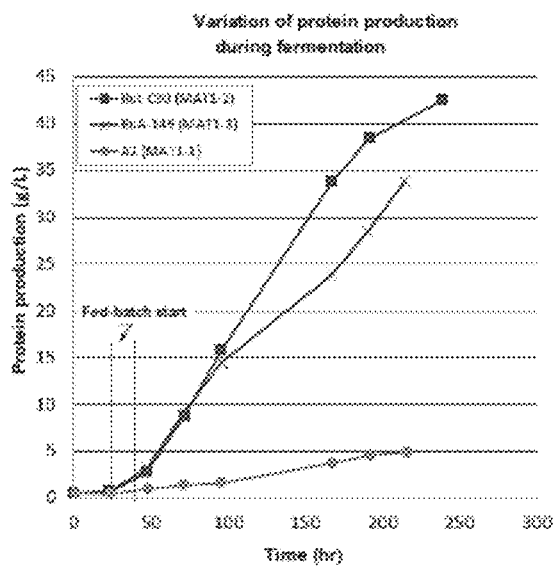
Figure 3B: Evaluation of quantity of proteins produced during fermentation in a DASGIP bioreactor

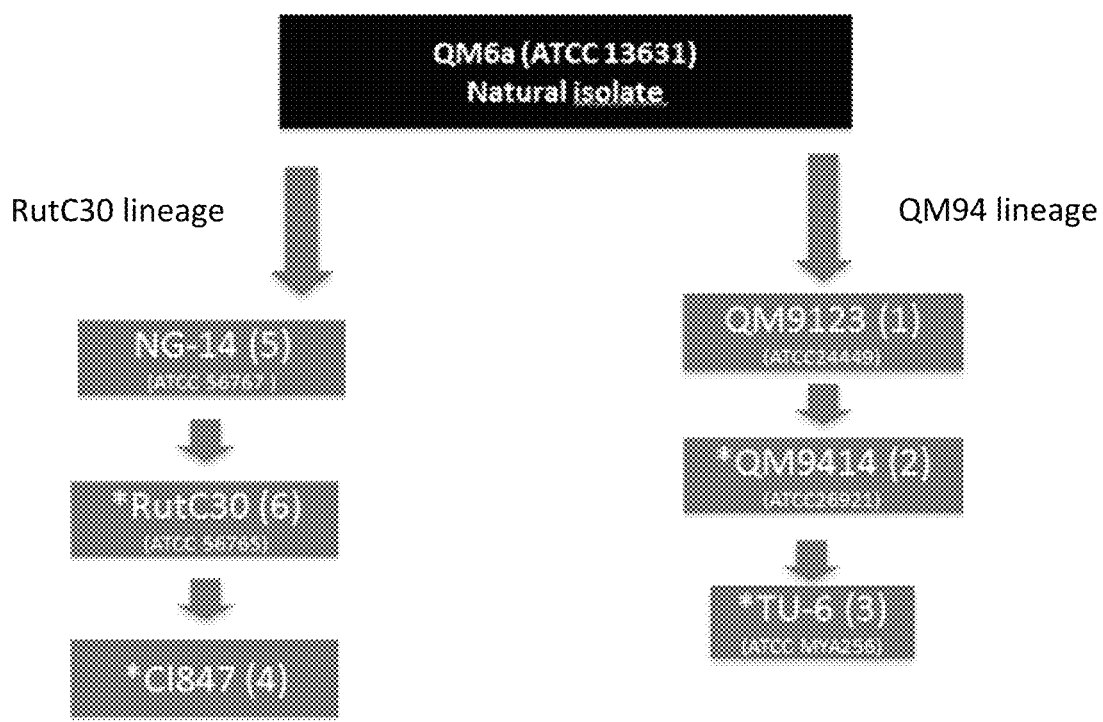
Figure 4: Genealogy of strains obtained from the strain QM6a

HYPER-PRODUCING TRICHODERMA REESEI STRAIN HAVING AN ENHANCED BETA-GLUCOSIDASE ACTIVITY

The present invention relates to a *Trichoderma reesei* strain which is hyper-producing and which has enhanced β-glucosidase activity, as well as the use of said strain.

*Trichoderma reesei* (*T. reesei*) is a cellulolytic filamentous fungus species, of the *Trichoderma* genus, which was discovered during World War II in the South Pacific. This fungus has the ability to secrete a large quantity of cellulosic enzymes (cellulases and hemicellulases), and it is currently essentially used in the production process of second-generation biofuels. Indeed, the enzymes produced by this fungus are particularly useful for converting plant biomass materials into bioproducts useful for industry, such as bioethanol.

Second-generation biofuels (derived from non-food resources) are particularly of interest at the present time, given that first-generation biofuels (derived from food resources) can only be produced in limited quantities, insofar as they compete with food production.

The production process of second-generation biofuels comprises four main steps: pretreatment of the lignocellulosic biomass, enzymatic hydrolysis of the lignocellulosic biomass, fermentation and distillation.

Although all the steps of the production of second-generation biofuels can and must be optimised—so as to increase production—, particular effort is focused on the enzymatic hydrolysis step. This hydrolysis step involves cellulase type enzymes produced by the filamentous fungus *T. reesei*.

More generally, *T. reesei* may be used as a platform strain for the production of homologous or heterologous proteins of interest. In order to optimise the performances of *T. reesei*, it is essential to enhance the *T. reesei* strains producing proteins of interest.

Among the enhancement methods envisaged, genetic engineering of *T. reesei* is thus a solution. It makes it possible to enhance the secretion performances of the cellulase-producing filamentous fungus, the enzyme properties and control the stability of the strains under industrial conditions.

Mutagenesis is a technique commonly used in genetic engineering. It aims to voluntarily introduce mutations into DNA so as to create genetically modified genes. This may make it possible to generate strains with interesting characteristics from an industrial point of view. There are two mutagenesis methods routinely used for introducing mutations into *T. reesei*: random mutagenesis and directed mutagenesis.

Random mutagenesis consists of inducing non-targeted mutations, anywhere in the DNA. These mutations are triggered by exposing the target organism to mutagenic chemical agents or to radiations. Given that mutations are a natural phenomenon, random mutagenesis is therefore considered as an accelerator of this natural process and the organisms thereby obtained are considered to be natural and not as genetically modified organisms (GMOs); therefore, they are not subject to the traceability requirement. However, this method induces, in addition to the mutation responsible for the characteristic of interest, a large number of undesirable so-called "collateral" mutations which contribute, by accumulating, to the instability, poor health, or even deadliness of the mutated organism.

Directed mutagenesis makes it possible to introduce identified mutations into a specific gene. For this purpose, the DNA of interest containing the mutations is synthesised and then introduced into the cell to be mutated where the DNA repair mechanism takes care of integrating same into the genome. The use of a selection marker makes it possible to identify the cells having integrated the mutation from those which have not integrated same. However, the organisms having undergone this mutagenesis are considered as GMOs (due to the introduction of exogenous DNA), and are therefore subject to a traceability requirement.

In the case of the use of *T. reesei* for the production of second-generation biofuels, the enhancement of the hydrolysis step, via the introduction of (random or directed) mutations into *T. reesei* is therefore not satisfactory, due to the accumulation of undesirable mutations caused, or indeed due to the introduction of exogenous DNA. Therefore, there is a need for a novel method for enhancing the hydrolysis step.

To date, the sexual reproduction of *T. reesei* has never been used as an enhancement tool as *T. reesei* has always been considered as not being capable of sexual reproduction. Nevertheless, the discovery of sexuality in *T. reesei* (Seidl et al., 2009) has opened up new possibilities in respect of the genetic enhancement of the strains. Sexual reproduction makes it possible, inter alia, to create genetic diversity, retain beneficial mutations and remove "collateral" mutations from the genome. The inventors of the present invention thus sought to develop the cellulolytic performances of *T. reesei* by means of sexual reproduction, particularly by crossing wild strains and industrial strains of *T. reesei*.

The present invention is thus based on the findings of the inventors who had the major merit of obtaining, after numerous tests, a novel *T. reesei* strain which hyper-produces cellulolytic enzymes. As stated in example 1, this strain was obtained by crossing and the cellulase hyper-producing strain RutC30 (Montenecourt and Eveleigh, 1977) with the strain A2 (strain derived from an isolated ascospore originating from the self-fertile strain CBS999.97). Surprisingly, among the cellulolytic enzymes produced by the strain according to the invention, the enzyme β-glucosidase exhibits an enhanced activity (compared to the activity of the parents RutC30 and A2). The strain according to the invention is also of the MAT1-1 mating type and is fertile.

In a first aspect, the invention thus relates to a *T. reesei* strain deposited on 3 Aug. 2017 with CNCM under the number CNCM I-5221. This strain is referred to as RuA-149 in the examples and also denotes the "strain according to the invention". CNCM denotes the National Collection of Micro-organism Cultures of Institut Pasteur, located at 25 rue du Docteur Roux, F-75724 Paris cedex 15.

Said strain is advantageously a hyper-producing strain of cellulolytic enzymes, particularly a hyper-producing strain of cellulases such as endoglucanases, exoglucanases and glucosidases. More particularly, a "hyper-producing strain of enzymes" according to the invention denotes a strain wherein the production of cellulolytic enzymes, particularly cellulases, represents between 81% and 250% with respect to the of the strain RutC30 (the strain RutC30 being the reference hyper-producing strain (Montenecourt and Eveleigh, 1977)). The term "between 81% and 250%" denotes all the values between 81 and 250, for example 90, 100, 110, 120, 130, 140, 150, 160, 170, 180, 190, 200, 210, 220, 230 and 240. In one embodiment, the strain according to the invention produces approximately 30 g/L of proteins, and preferably approximately 34 g/L (assays conducted with the Lowry method, see Lowry et al.). The cellulase production by a strain may be determined using any routine techniques for those skilled in the art, such as for example the following protocol:

the strain is cultured in a microplate with 2 mL of cellulase induction medium (such as Avicel®, marketed by MSDS under the reference No.: 9004-34-6).

after seven days of culture, the cellulase production is measured by assaying the quantity of total proteins secreted in the supernatant according to the Bradford method. A correlation between total secreted proteins and cellulases may be made as, in *T. reesei*, the main exoglucanases (CBHI, CBHII) and endoglucanases (EGI, EGII) may represent up to 90% of the total quantity of proteins secreted (see for example Markov et al., 2005).

Advantageously, said strain according to the invention also has an enhanced β-glucosidase activity. The term "enhanced β-glucosidase activity" denotes a superior β-glucosidase activity with respect to the strain RutC30 (ATCC® 56765), preferably approximately three times greater than the β-glucosidase activity of RutC30. According to one embodiment, said strain has a β-glucosidase activity of at least 0.53 IU/mg, and preferably of at least 1.33±0.09 IU/mg. Obtaining an enhanced β-glucosidase activity makes it possible to increase the performance of the enzyme cocktail (comprising endo/exoglucanases and glucosidases such as (β-glucosidase) as it consists of the limiting enzyme of cellulose degradation. The β-glucosidase activity may be determined using any routine techniques for those skilled in the art, such as for example the hydrolysis of p-nitrophenyl-β-Dglucopyranoside (pNPG) described hereinafter:

the assay of the β-glucosidase activity is performed on the culture supernatant. The samples under assay are diluted in 50 mM citrate buffer supplemented with 0.5 g/L of Bovine Serum Albumin to obtain a protein concentration of the order of 50 to 100 mg/L;

10 μL of the dilution and 90 μL of pNPG substrate prepared to 5 mM in pH 4.8 50 mM citrate buffer are added into 1.5 mL tubes;

the tubes are incubated for 30 minutes to 50° C.;

100 μL of 2% Na2CO3 is added to the tubes;

after 20 minutes of incubation, the optical density (absorbance) is read at 410 nm;

the equivalent concentration of released p-nitrophenol is computed using a series of 25, 50, 100 and 200 μM of 50 mM citrate buffer supplemented with 0.5 g/L of BSA.

Said strain according to the invention is of the MAT1-1 mating type. This strain therefore has the advantage of being compatible with all industrial strains. Indeed, all industrial strains having been generated from the natural isolate QM6a which is of the MAT1-2 mating type, they are all of the MAT1-2 sterile female but fertile male mating type.

Said strain according to the invention is also female fertile, i.e. it is capable of differentiating fructifications and systematically emitting ascospores (reproductive cells of ascomycetes fungi such as *T. reesei*) when crossed with a MAT1-2 sterile female strain. Said strain according to the invention is also fertile male.

Said strain according to the invention also has the advantage of not being considered as a genetically modified organism (GMO), and is therefore not subject to a traceability requirement.

According to one embodiment of the invention, said strain denotes an isolated and/or purified strain.

In a second aspect, the invention also relates to the use of a strain according to the invention, i.e. the use of a strain as defined above.

The invention thus relates to the use of a strain as defined above for the production of cellulolytic enzymes. According to the invention, the term "cellulolytic enzymes" more particularly denotes cellulase enzymes chosen from among endoglucanases, exoglucanases and glucosidases, and more particularly β-glucosidase. The term "cellulase" more particularly refers to an enzyme suitable for hydrolysing cellulose and enabling the micro-organisms (such as *T. reesei*) producing same to use cellulose as a source of carbon, by hydrolysing this polymer into simple sugars (glucose). The invention therefore also relates to the use of a strain as defined above for hydrolysing cellulose or lignocellulose into glucose.

The invention also relates to the use of the strain as defined above for producing biosourced products from glucose. According to the invention, the term "biosourced product" denotes any product which is not of fossil origin and which does not contain an organic product of fossil origin. The term "product of fossil origin" denotes any organic product derived from oil or coal or oil derivatives or coal derivatives. Preferentially, according to the invention, it consists of an alcohol, such as isopropanol, butanol or ethanol, and more particularly ethanol. According to one embodiment, the invention also relates to a method for producing biosourced products from glucose comprising the use of cellulolytic enzymes produced by a *Trichoderma reesei* strain as defined above. According to this embodiment, the invention thus relates to a step for contacting between glucose and the cellulolytic enzymes produced by a *Trichoderma reesei* strain as defined above.

The invention also relates to the use of a strain as defined above for producing biofuel. As such, the invention relates to a method for producing a biofuel from cellulosic or lignocellulosic substrates, comprising the use of the cellulolytic enzymes produced by a *Trichoderma reesei* strain as defined above. The invention also relates to a method for producing a biofuel from cellulosic or lignocellulosic substrates, comprising:

a pretreatment step of a cellulosic or lignocellulosic substrate so as to obtain a pretreated substrate, an enzymatic hydrolysis step of the pretreated substrate, in the presence of a mixture (or cocktail) of enzymes produced by a *T. reesei* strain as defined above and a suitable substrate, so as to obtain a hydrolysate, an alcoholic fermentation step of the hydrolysate obtained, a distillation step.

The conditions of each of the steps (temperatures, times, etc.) may be readily determined by those skilled in the art, similarly to the suitable substrate. For example, lactose or cellulose, or mixtures thereof, are substrates conventionally used to induce cellulase production by *T. reesei*, although further substrates may be envisaged. According to one embodiment of the invention, in the method for producing a biofuel, the *T. reesei* strain serves to produce the cellulolytic enzymes. According to the invention, the term "biofuel" denotes any product derived from the processing of biomass and suitable for use for energy purposes. By way of example, this denotes biogases, products suitable for being incorporated (optionally after subsequent processing) in a fuel or being a fuel in its own right, such as alcohols (non-exclusively ethanol, butanol and/or isopropanol), solvents (acetone), acids (butyric), lipids and derivatives thereof (short or long-chain fatty acids, fatty acid esters), as well as hydrogen. Preferably, the biofuel according to the invention is an alcohol, for example ethanol, butanol and/or isopropanol. More preferentially, the biofuel according to the invention is ethanol. In one particular embodiment, said method for producing a biofuel comprises a step for recovering the biofuel produced.

In one particular embodiment, the invention also relates to a method for producing β-glucosidase comprising the step for culturing a T. reesei strain as defined above in a culture medium comprising a suitable substrate, particularly chosen among lactose and cellulose or one of the mixtures thereof. In one particular embodiment, said method for producing β-glucosidase may comprise a step for recovering β-glucosidase.

In a third aspect, the invention also relates to a sexual reproduction method between two Trichoderma reesei strains, said method comprising a step for crossing between a first strain as defined above and a second compatible strain. T. reesei is a so-called bipolar heterothallic fungus, i.e. that sexual reproduction is only possible between individuals of compatible mating types (MAT1-1 and MAT1-2). According to the invention, "a second compatible strain" thus denotes a T. reesei strain of MAT1-2 mating type. Advantageously, the "second compatible strain" is sterile female and fertile male. According to one preferred embodiment, the second compatible strain is chosen among the strains NG-14 (ATCC 56767), RutC30 (ATCC 56765), C1847, QM9414 (ATCC 26921), QM9123 (ATCC 24449), and Tu-6 (ATCC MYA256), preferably the strains RutC30, C1847, QM9414 and Tu-6. These strains are well-known to those skilled in the art. The strain according to the invention may be used to produce crosses with other industrial strains derived from mutagenesis—so as to enhance same—, but also with strains derived from genetic engineering—for example so as to eliminate selection markers or indeed to combine characteristics/properties of interest—. In other words, the sexual reproduction method according to the invention enables advantageously (i) non-GMO enhancement of industrial strains of T. reesei by sexual reproduction, but also (ii) elimination of selection markers by crossing this strain with a GMO industrial strain or (iii) obtaining new strains with the properties/characteristics of interest. The strain according to the invention may thus be considered as a "tool" strain and may be crossed with other industrial strains so as to enhance the performances thereof. In one aspect, the invention thus relates to the use of a T. reesei strain as defined above for enhancing the properties of a compatible strain, particularly industrial. The term "compatible strain" denotes a T. reesei strain of MAT1-2 mating type, particularly sterile female and fertile male. The term "industrial strain" denotes a strain derived from the strain QM6a; in other words a sterile female and fertile male strain. The term "enhancing the properties of an industrial strain" means that crossing between the strain according to the invention and a compatible strain, particularly industrial, makes it possible to obtain and/or select progeny having enhanced properties. In other words, the strain according to the invention may be used, for enhancing by crossing with a compatible strain, particularly industrial, the properties of the new strain obtained. The term "enhanced properties" may denote a superior viscosity, superior productivity, superior stability, etc. The viscosity of a strain may be determined using any routine techniques for those skilled in the art, such as for example the protocol described by N. Hardy et al. The stability of a strain may also be determined using any routine techniques for those skilled in the art, such as for example the protocol described by N. Hardy et al. According to the invention, the "stability of a strain" denotes the preservation over time of the properties such as the productivity, composition of the enzyme cocktail, morphology, etc.

The invention will be better illustrated by the following examples and figures. The examples hereinafter are intended to elucidate the subject matter of the invention and illustrate advantageous embodiments, and are in no way intended to restrict the scope of the invention.

FIGURES

FIG. 1 represents fed-flask protein production.
FIG. 2 represents the principle of the IFP Énergies nouvelles cellulase production process.
FIG. 3A represents the evaluation of the quantity of biomass during fermentation in a DASGIP bioreactor.
FIG. 3B represents the evaluation of the produced quantity of proteins produced during fermentation in a DASGIP bioreactor.
FIG. 4 represents the genealogy of the strains obtained from the strain QM6a. The strains marked with an asterisk were tested by crossing with the strain RuA149 (see example 2). The references of the strains shown in the Figure are as follows:
(1) Mandels, M., Weber, J., & Parizek, R. (1971). Enhanced cellulase production by a mutant of Trichoderma viride. Applied microbiology, 21(1), 152-4.
(2) Mandels M. (1975). Microbial sources of cellulase. Biotechnol Bioeng. 5, 81-105.
(3) Gruber, F., Visser, J., Kubicek, C. P., & De Graaff, L. H. (1990). The development of a heterologous transformation system for the cellulolytic fungus Trichoderma reesei based on a pyrG-negative mutant strain. Current genetics, 18(1), 71-6.
(4) Durand, H., Clanet, M., & Tiraby, G. (1988). Genetic improvement of Trichoderma reesei for large scale cellulase production. Enzyme and microbial technology, 10 (June), 341-346.
(5) Eveleigh D E, Montenecourt B S (1979) Increasing yields of extracellular enzymes. Adv Appl Microbiol 25:57-74.
(6) Montenecourt B S, Eveleigh D E (1977). Preparation of Mutants of Trichoderma reesei with Enhanced Cellulase Production. Applied and environmental microbiology, 34(6), 777-782.

EXAMPLES

Example 1: Preparation of the Strain According to the Present Invention (i.e. the Strain as Deposited Under the Number CNCM I-5221) and Determining the Characteristics Thereof 1. Preparation The cellulase hyper-producing strain RutC30 (or RutC30) (Montenecourt and Eveleigh, 1977) was crossed with the strain A2 according to the protocol described in Seidl et al. The strain RutC30 (deposited at ATCC under the number 56765) was obtained by means of three mutagenesis steps from the strain QM6a and is one of the best producers of cellulases in the public domain (Peterson and Nevalainen, 2012).

After crossing, a plurality of ascospore isolation campaigns were carried out. 295 purified descendants were obtained. The latter were then subject to screening in three steps. These successive screens make it possible to reduce the number of candidates from a few hundred to the individual with the highest performance for cellulase production.

2. Cellulase Production—Microplate Test

The first screening step is based on a method for measuring the production of extracellular proteins using the Bradford method making it possible to rank the candidates and intended to reduce the number thereof drastically so as to only transfer to the second step around ten individuals of the most interest.

The second screen is based on a miniaturisation of the industrial conditions (Jourdier et al., 2012) and makes it possible to select a few individuals for which the performances will be tested in bioreactors.

During the first screen, the descendants are cultured in a microplate in 2 mL of cellulase induction medium (such as Avicel®, marketed by MSDS under the reference No.: 9004-34-6).

After seven days of culture, the cellulase production is measured by assaying the quantity of total proteins secreted in the supernatant according to the Bradford method. A correlation between total secreted proteins and cellulases may be made as in $T.$ $reesei$, the main exoglucanases (CBHI, CBHII) and endoglucanases (EGI, EGII) may represent up to 90% of the total quantity of proteins secreted (Markov et al. 2005).

Only the ten best producers of cellulases, exhibiting a standard deviation less than 10%, were selected.

3. Cellulase Production—Miniaturisation of Industrial Conditions

The ten best producers of cellulases were selected to be subjected to a second screen which uses the "fed-flask" protocol developed by Jourdier et al., 2012 and which is based on the miniaturisation of a fed-batch protocol suitable for maximising the enzyme production (Jeude et al., 2006). This protocol makes it possible to produce cellulases in a flask with a controlled feed with a stoichiometric mixture of carbonated substrate and NH3 base, which makes it possible to stabilise the pH of the culture without a pH control system. An incubator with a rotary stirrer is used to control the stirring and the temperature (Jourdier et al., 2012).

The fed-flask methodology makes it possible to test eight strains in parallel. Each flask is fed by pumps with a flow rate of 0.3 mL/hr with a solution containing 50 g/L of lactose, 0.8 g/L of (NH4)2SO4, and 160 mM NH3. At 96 hrs, the total secreted proteins are assayed. The results of the strains QM6A, A2, RutC30 and RuA-149 are shown in FIG. 1. The fed-flask protein production was only evaluated once for all the strains except for the reference strain RutC30. The percentages represent the rate of protein production with respect to the reference strain RutC30.

This production method makes it possible to rank the strains according to their production of secreted proteins which correspond in $T.$ $reesei$ to cellulases (Markov et al., 2005). After a fed-batch process in lactose for 96 hrs, the assay of the proteins produced measured according to the Lowry method (FIG. 1) confirms that the strain A2 produces more proteins than the strain QM6a and two times less than the hyper-producing strain RutC30.

By means of this second screen, the strain RuA-149 was selected to be tested in bioreactors mimicking industrial conditions on a small scale. The bioreactor culture is carried out according to the IFP Énergies nouvelles production protocol (Pourquie et al., 1988) which distinguishes two phases (FIG. 2):

a batch phase of approximately 30 hours which corresponds to a growth phase of $T.$ $reesei$ which produces biomass until total glucose consumption;

a fed-batch phase of approximately 200 hours during which cellulase production is induced by adding lactose at a constant rate so as to maximise and keep constant the production rate.

The production of biomass (FIG. 3A) and proteins (FIG. 3B) (assays with the Lowry method) were evaluated throughout the fermentation in DASGIP bioreactors. The specific Filter Paper (FP) (endoglucanase and exoglucanase activity) and β-glucosidase activities are assayed only for the final samples (after 200 hours). These experiments were repeated twice and the results obtained are similar.

The results are shown in Table 1 hereinafter.

TABLE 1

Specific Filter Paper (FP) and β-glucosidase activities of parent strains (A2, RutC30 and of progeny RuA-149).

| Strain | FP activity (IU/mg) | β-glucosidase activity (IU/mg) |
|---|---|---|
| RutC30 | 0.77 ± 0.11 | 0.45 ± 0.07 |
| A2 | 0.41 ± 0.01 | 0.72 ± 0.03 |
| RuA-149 | 0.8 ± 0.13 | 1.33 ± 0.09 |

The strain RuA-149 progressively produces approximately 5 g/L of biomass until total glucose consumption which occurs after 34 hrs. During the fed-batch phase, the biomass is stabilised around 15 g/L (FIG. 3A).

The production of proteins by the strain RuA-149 starts once induction has been carried out but it slows down from 100 hrs. The protein production of the strain RuA-149 is of 34 g/L (FIG. 3B).

Effective cellulose hydrolysis requires the synergistic action of endoglucanases, exoglucanases and β-glucosidases (Kubicek et al., 2009). Endoglucanases and exoglucanases may represent up to 90% of the total quantity of secreted proteins whereas β-glucosidase represents less than 1% (Lynd et al., 2002; Herpoel-Gimbert et al., 2008). The main β-glucosidase (encoded by the gene bgl1 or cel3a in $T.$ $reesei$) is involved for hydrolysing cellobiose (dimer) during the final step prior to obtaining the glucose monomer (Chauve et al., 2010). The small proportion thereof in the cellulolytic cocktail of $T.$ $reesei$ induces an accumulation of cellobiose the inhibitory effect whereof on exoglucanases induces a significant slowdown of hydrolysis (Chauve et al., 2010). An increase in the β-glucosidase activity in the enzyme cocktail is essential for more effective hydrolysis during second-generation bioethanol production.

At the end of fermentation, the quality of the enzyme cocktail produced is evaluated by measuring the enzyme activities (FIGS. 3A and 3B). The endoglucanase and exoglucanase activity is assayed by means of the FP (filter-paper) test which gives an indication of the overall effectiveness of the cellulase cocktail (Ghose, 1987). The limiting activity of β-glucosidase is evaluated separately by measuring the hydrolysis of p-nitrophenyl-β-Dglucopyranoside (pNPG).

The FP assay demonstrates that the strain A2 has a low specific cellulolytic activity with respect to the reference strain RutC30 but the β-glucosidase activity thereof is almost two times greater than that of RutC30. The strain according to the invention, RuA-149, has a similar overall FP activity to that of the reference strain RutC30 but it has an approximately three times greater β-glucosidase activity.

These results demonstrate that the cross between the strain A2 and the hyper-producing strain RutC30 made it possible to generate an enhanced hyper-producing strain for the β-glucosidase activity.

Example 2: Preparation of Fertile Cross Between the Strain According to the Present Invention (i.e. the Strain as Deposited Under the Number CNCM I-5221) with Sterile Female MAT1-2 Strains The strain RuA-149 was crossed with MAT1-2 sterile female *Trichoderma reesei* MAT1-2 derived from the isolate QM6a. The MAT1-1 IDC1 strains A2 and QM6a (Linke et al., 2015) were used as a positive control (fertile cross). The crosses are produced by confrontation: the strains were inoculated in mutually facing rows, with approximately 1.5 cm between the two strains. Each row contains four to six inoculums of the same strain from either a plate of conidia or a cryotube. A cross is fertile when ascospores are expelled from the perithecia contained in the stromata. The expulsion of ascospores is observed by the presence of a yellowish substance present in the ostioles of the perithecia. The crosses were produced with the strains RutC30, C1847, QM9414 and Tu-6. The results are given in Table 2 hereinafter. The genealogy of the strains tested is shown in FIG. 4.

TABLE 2

Cross between the strain according to the invention and sterile female MAT1-2 strains

| Strains tested (sterile female MAT1-2) | Cross with A2 (positive control) | Cross with strain RuA-149 |
|---|---|---|
| RutC30 | Fertile | Fertile |
| C1847 | Fertile | Fertile |
| QM9414 | Fertile | Fertile |
| Tu-6 | Fertile | Fertile |

These results confirm that the strain according to the invention may be crossed with fertile female strains, and thereby generate new strains.

REFERENCES

Bradford, M. (1976). A rapid and sensitive method for the quantitation of microgram quantities of protein utilizing the principle of protein-dye binding. Analytical Biochemistry 72, 248-254.

Chauve, M., Mathis, H., Huc, D., Casanave, D., Monot, F., and Lopes Ferreira, N. (2010). Comparative kinetic analysis of two fungal beta-glucosidases. Biotechnology for biofuels 3, 3.

Ghose, T. K. (1987). Measurement of cellulase activities. Pure and Applied Chemistry 59.

Herpoël-Gimbert, I., Margeot, A., Dolla, A., Jan, G., Mollé, D., Lignon, S., Mathis, H., Sigoillot, J., Monot, F., and Asther, M. (2008). Comparative secretome analyses of two *Trichoderma reesei* RUT-C30 and CL847 hypersecretory strains. Biotechnology for biofuels 1, 18.

Jeude, M., Dittrich, B., Niederschulte, H., Anderlei, T., Knocke, C., Klee, D., and Büchs, J. (2006). Fed-batch mode in shake flasks by slow-release technique. Biotechnology and bioengineering 95, 433-445.

Jourdier, E., Poughon, L., Larroche, C., Monot, F., and Ben Chaabane, F. (2012). A new stoichiometric miniaturization strategy for screening of industrial microbial strains: application to cellulase hyper-producing *Trichoderma reesei* strains. Microbial cell factories 11, 70.

Kubicek, C. P., Mikus, M., Schuster, A., Schmoll, M., and Seiboth, B. (2009). Metabolic engineering strategies for the improvement of cellulase production by Hypocrea jecorina. Biotechnology for biofuels 2, 19.

Hardy N., Moreaud M., Guillaume D., Augier F., Nienow A., Béal C., Ben Chaabane F., (2017). Advanced digital image analysis method dedicated to the characterization of the morphology of filamentous fungus. Journal of Microscopy. 266, 2, 126-140.

Linke R., Thallinger G., Haarmann T., Eidner J., Schreiter M., Lorenz P., Seiboth B., Kubicek C., (2015). Restoration of female fertility in *Trichoderma reesei* QM6a provides the basis for inbreeding in this industrial cellulase producing fungus. Biotechnol Biofuels. 2015; 8: 155

Lowry O H, Rosebrough N J, Farr A L, Randall R J, (1951). Protein measurement with the Folin phenol reagent. J Biol Chem, 193:265-275.

Lynd, L. R., Weimer, P. J., van Zyl, W. H., and Pretorius, I. S. (2002). Microbial Cellulose Utilization. Fundamentals and Biotechnology. Microbiology and molecular biology reviews 66, 506-577.

Markov, A. V., Gusakov, A. V., Kondratyeva, E. G., Okunev, O. N., Bekkarevich, A. O., and Sinitsyn, A. P. (2005). New Effective Method for Analysis of the Component Composition of Enzyme Complexes from *Trichoderma reesei*. Biochemistry (Moscow) 70, 657-663.

Montenecourt, B. S., and Eveleigh, D. E. (1977). Preparation of mutants of *Trichoderma reesei* with enhanced cellulase production. Applied and environmental microbiology 34.

Peterson, R., and Nevalainen, H. (2012). *Trichoderma reesei* RUT-C30—thirty years of strain improvement. Microbiology 158, 58-68.

Pourquie, J., Warzywoda, M., Chevron, F., Thery, D., and Lonchamp, D. (1988). Scale up of cellulase production and utilization. In FEMS Symposium n°43: Biochemistry and Genetics of Cellulose Degradation., J.-P. Aubert, P. Beguin and J. Millet, eds., pp. 71-86.

Seidl, V., Seibel, C., Kubicek, C. P., and Schmoll, M. (2009). Sexual development in the industrial workhorse *Trichoderma reesei*. Proceedings of the National Academy of Sciences of the United States of America 106, 13909-13914.

The invention claimed is:
1. A *Trichoderma reesei* strain deposited with Collection Nationale de Cultures de Microorganismes (CNCM) under the Accession Number CNCM I-5221.
2. A method for producing β-glucosidase, comprising: culturing the *Trichoderma reesei* strain of claim 1 in a culture medium comprising a suitable substrate and recovering the β-glucosidase from the culture medium.

* * * * *